US00RE35014E

United States Patent [19]

Yoshino et al.

[11] E Patent Number: Re. 35,014

[45] Reissued Date of Patent: Aug. 8, 1995

[54] COMPOSITION OF POLYARYLATE, POLYAMIDE, POLYETHYLENE TEREPHTHALATE AND EPOXY RESIN

[75] Inventors: Kenji Yoshino; Kazuya Takemura; Tadahiro Wakui, all of Chiba, Japan

[73] Assignee: Kawasaki Steel Corporation, Japan

[21] Appl. No.: 102,769

[22] Filed: Aug. 6, 1993

Related U.S. Patent Documents

Reissue of:

[64] Patent No.: 5,037,900
Issued: Aug. 6, 1991
Appl. No.: 450,222
Filed: Dec. 12, 1989

U.S. Applications:

[62] Division of Ser. No. 412,900, Sep. 26, 1989, abandoned.

[30] Foreign Application Priority Data

Sep. 30, 1988 [JP] Japan ..... 63-246656
Dec. 26, 1988 [JP] Japan ..... 63-328719

[51] Int. Cl.[6] ..... C08L 67/02; C08L 77/02; C08L 77/04; C08L 77/06

[52] U.S. Cl. ..... 525/423; 525/111

[58] Field of Search ..... 525/423

[56] References Cited

U.S. PATENT DOCUMENTS 4,777,223 10/1988 Robeson ..... 525/423
4,820,771 4/1989 Müssig et al. ..... 525/423

FOREIGN PATENT DOCUMENTS 227053 10/1988 European Pat. Off. .
291997 11/1988 European Pat. Off. .
55-78051 6/1980 Japan ..... 525/423

OTHER PUBLICATIONS

Lee and Neville, Handbook of Epoxy Resins, McGraw-Hill Book Co., New York, N.Y., 1967, pp. 4–6.

*Primary Examiner*—Robert E. Sellers
*Attorney, Agent, or Firm*—Austin R. Miller

[57] ABSTRACT

Thermoplastic resin compositions comprising polyarylate and polyamide resins as main components, polyethylene terephthalate and an epoxy resin of the following formula [1] in a predetermined amount are provided.

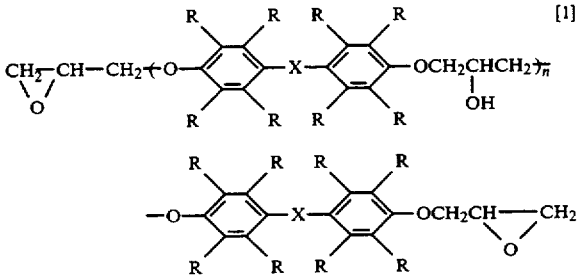

[1]

The thermoplastic resin compositions of the invention have good impact strength along with good heat and solvent resistances and good moldability.

3 Claims, No Drawings

COMPOSITION OF POLYARYLATE, POLYAMIDE, POLYETHYLENE TEREPHTHALATE AND EPOXY RESIN

Matter enclosed in heavy brackets [ ] appears in the original patent but forms no part of this reissue specification; matter printed in italics indicates the additions made by reissue.

This is a division of U.S. application Ser. No. 412,900, filed Sept. 26, 1989, now abandoned.

BACKGROUND OF THE INVENTION

This invention relates to thermoplastic resin compositions which are mainly composed of polyarylate resins, polyamide resins and epoxy resins and have excellent impact strength, heat and solvent resistances and moldability.

Compositions made of polyarylate resins and polyamide resins have good heat and solvent resistances and good moldability. For instance, Japanese Patent Publication No. 56-14699 discloses a resin composition made of a polyarylate and a polyamide, and Japanese Laid-open Patent Application No. 52-100552 discloses a resin composition which is made of a polyarylate-based resin composed of a mixture of a polyarylate and polyethylene terephthalate, and a polyamide.

Since polyarylates and polyamides are substantially immiscible with each other, the composition obtained by melt kneading exhibits a phase separation structure wherein the adhesion strength at the interface between the polyarylate phase and the polyamide phase is so weak, with the attendant disadvantage of the resulted composition that the impact strength becomes small, thus leading to brittleness.

Attempts have been made to improve the impact strength of the resin compositions made of polyarylates and polyamides by addition, as the third ingredient, of a miscibility improver or an impact strength improver. For instance, in Japanese Laid-open Patent Application, there is used an N-substituted amido-containing polymer as the third ingredient. As the third ingredient, there are used polyalkylene phenylene esters containing a group of sulfonate salt in Japanese Laid-open Patent Application No. 59-105050, glycidyl group-containing olefin copolymers in Japanese Laid-open Patent Application No. 61-183353, mixtures of epoxy group-containing ethylene copolymers and acid anhydride-containing olefin copolymer in Japanese Laid-open Patent Application Nos. 62-277462 and 62-283146.

However, the resin compositions disclosed in the Japanese Laid-open Patent Application Nos. 58-67749 and 59-105050 are far from satisfactory in improving the impact strength. With the resin compositions disclosed in the Japanese Laid-open Patent Application Nos. 61-183353, 62-277462 and 62-283146, the effect of improving the impact strength starts to develop when the content of the third ingredient exceeds about 5 wt %. For obtaining satisfactory impact strength, the third ingredient has to be added in amount ranging from 10 to 30 wt%. Such resin compositions are unfavorably apt to undergo thermal decomposition in the cylinder of an extruder or injection molding machine, with attendant disadvantages such as gelation, coloration, a lowering of mechanical strength, and defects in appearance of the resultant moldings such as flow mark, silver streak and silver blister. Moreover, since olefin polymers are formulated in large amounts, the resulting resin compositions is improved in the impact strength but is considerably lowered with respect to the tensile strength, bending strength, modulus of elasticity and heat resistance.

A resin compositions made of a polyarylate resin, a polyethylene terephthalate resin and a polyamide resin has excellent heat and solvent resistances and moldability and is disclosed, for example, in Japanese Patent Publication No. 58-50260. However, this resin composition has such problems as involved in the compositions made of polyarylate resins and polyamide resins. More particularly, although polyarylates and polyethylene terephthalate are miscible with each other, polyamide is incompatible with these resins. The composition obtained by melt kneading of these resins exhibits a phase separation structure wherein the adhesion strength at the interface between the polyarylate and polyethylene terephthalate phases and the polyamide phase is weak, so that the composition has inconveniently a small impact strength and is brittle.

In order to improve the impact strength of the above composition, Japanese Laid-open Patent Application No. 52-100552 proposed an improved process, but satisfactory mechanical strength has not yet been obtained.

Japanese Patent Public Disclosure No. 187761/1987 discloses a thermoplastic resin composition comprising polycarbonate, poly(ester carbonate) and polyamide, in which bisphenol A diglycidyl ether is contained as a compatibilizer having an epoxy group.

However, the composition disclosed in Japanese Patent Public Disclosure No. 187761/1987 is chiefly composed of polycarbonate. Polycarbonate is decomposed easily by heat in the presence of even a small quantity of basic substance. In kneading process of polycarbonate and polyamide, therefore, polycarbonate is decomposed during thermal melting caused by the amide bond and terminal amino group of polyamide. In addition, since a monomer such as bisphenol A diglycidyl ether is used as the compatibilizer, it is difficult to knead such a liquid monomer with resins which are solid at normal temperatures.

SUMMARY OF THE INVENTION

An object of the invention is to provide a resin composition which has remarkably improved impact strength without a sacrifice of good solvent and heat resistances, good moldability, high rigidity and good thermal stability inherent to thermoplastic resin compositions predominantly made of polyarylates and polyamides.

According to the present invention, there is provided a thermoplastic resin composition which comprises a main component comprised of a polyarylate resin and a polyamide resin, and an epoxy resin of the following formula [1] contained in the main component in a predetermined amount

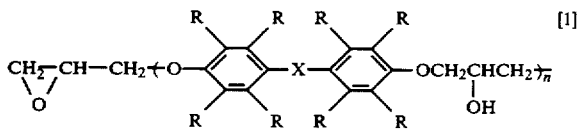

[1]

-continued

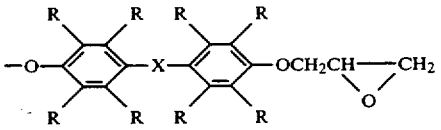

wherein X represents a direct bond, a lower alkylene group having from 1 to 4 carbon atoms, *a lower alkylidene group having from* 1 to 4 carbon atoms,

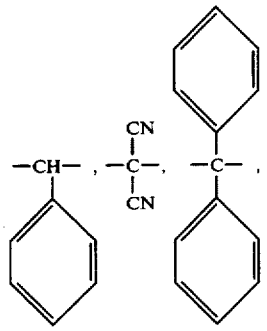

$—SO_2—$, —O—, or —S— wherein part or all of the hydrogen atoms of X may be substituted with a halogen atom if X represents any hydrocarbon defined above, R's independently represent a hydrogen atom, a halogen atom, a lower alkyl group having from 1 to 4 carbon atoms, and n is an integer of or over.

DETAILED DESCRIPTION OF THE INVENTION

A first aspect of the invention is initially described.

According to the first aspect of the invention, there is provided a thermoplastic resin composition which comprises:

100 parts by weight of a mixture of from 10 to 90 wt % of a polyarylate-based resin containing not less than 70 wt % of a polyarylate resin component and, correspondingly, from 90 to 10 wt % of a polyamide-based resin containing not less than 70 wt % of a polyamide resin component; and from 0.1 to 15 parts by weight of an epoxy resin of the following general formula

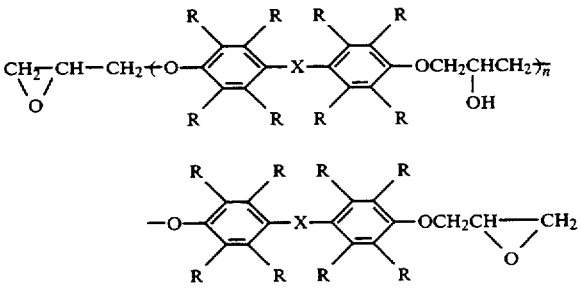

wherein X represents a direct bond, a lower alkylene group having from 1 to 4 carbon atoms, *a lower alkylidene group having from* 1 to 4 carbon atoms,

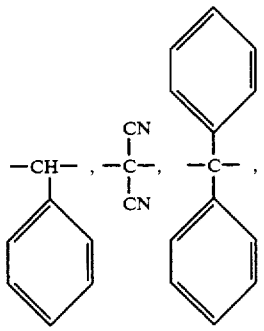

$—SO_2—$, —O—, or —S— wherein part or all of the hydrogen atoms of X may be substituted with a halogen atom if X represents any hydrocarbon defined above, R's independently represent a hydrogen atom, a halogen atom, a lower alkyl group having from 1 to 4 carbon atoms, and n is an integer of or over.

The polyarylate-based resin used in the present invention should contain not less than 70 wt % of a polyarylate resin component which is prepared from a bisphenol and/or its derivative, terephthalic acid and/or its derivative and isophthalic acid and/or its derivative and consists of these three ingredients.

Terephthalic acid and isophthalic acid have, respectively, the following formulae

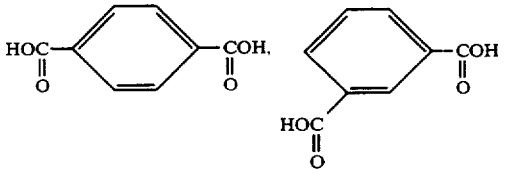

The derivatives of terephthalic acid and isophthalic acid include acid halide compounds such as terephthalic acid dichloride, isophthalic acid dichloride and the like, and diester compounds such as dimethyl terephthalate, dimethyl isophthalate, diphenyl terephthalate, diphenyl isophthalate and the like.

Terephthalic acid, isophthalic acid and derivatives thereof may be substituted, at part or all of the hydrogen atoms of the phenylene group, with a halogen atom or a lower alkyl group.

The bisphenols and derivatives thereof are represented by the following formula [2]

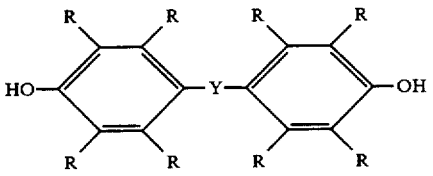

[2]

wherein Y represents a lower alkylene group having from 1 to 4 carbon atoms, *a lower alkylidene group having from* 1 to 4 carbon atoms,

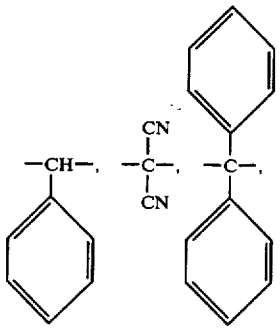

$-SO_2-$, $-O-$, $-S-$ or $-\underset{\underset{O}{\|}}{C}-$, wherein part or all of the hydrogen atoms in Y, if any, may be substituted with a halogen atom, and R's independently represent a hydrogen atom, a halogen atom or a lower alkyl group having from 1 to 4 carbon atoms.

Examples of the bisphenols of the formula [2] include 2,2-bis(4-hydroxyphenyl)propane, bis(4-hydroxyphenyl)methane, 4,4'-dihydroxydiphenyl ether, bis(4-hydroxyphenyl)sulfide, bis(4-hydroxyphenyl)sulfone, bis(4-hydroxyphenyl)ketone, bis(4-hydroxy-3-methylphenyl)methane, bis(4-hydroxy-3,5-dibromophenyl)methane, 1,1-bis(4-hydroxyphenyl) ethane, 2,2-bis(4-hydroxy-3-methyl-phenyl)propane, 2,2-bis(4-hydroxy-3,5-dimethylphenyl)propane, 2,2-bis(4-hydroxy-3,5-dichlorophenyl) propane, 2,2-bis(4-hydroxy-3,5-dibromophenyl)propane, 2,2-bis(4-hydroxyphenyl)butane, bis(4-hydroxyphenyl)-phenylmethane bis(4-hydroxyphenyl)diphenylmethane, bis(4-hydroxyphenyl)difluoromethane and the like. Of these, 2,2-bis(4-hydroxyphenyl)propane which is usually called bisphenol A is preferred because of the ease in availability of starting materials. If necessary, a small amount of aromatic dihydroxy compounds such as, for example, 4,4'-biphenol, 2,6-naphthalenediol, hydroquinone, chlorohydroquinone and the like, may be used in combination with the bisphenols.

The polyarylate resins may be prepared by any methods including an interfacial polymerization method, a solution polymerization method and a melt polymerization method.

The polyarylate-based resins containing components other than the above-described polyarylate resin components include the following mixtures and such polyarylate-based resins are, of course, within the scope of the invention provided that the polyarylate resin component consisting of the aforesaid three ingredients is contained in amounts not less than 70 wt %.

Mixture of the polyarylate resin and polybutylene terephthalate.

Mixture of the polyarylate resin and the polysulfone resin of the recurring units of the following formula

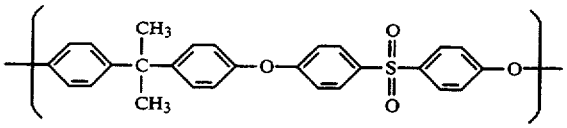

Mixture of the polyarylate resin and the polycarbonate resin of the recurring units of the following formula

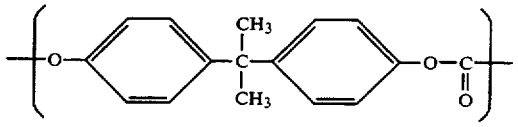

Mixture of the polyarylate resin and the polyphenylene sulfide of the recurring units of the following formula

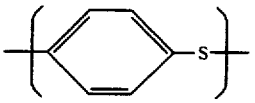

Mixture of the polyarylate resin and the polyphenylene oxide resin of the recurring units of the following formula

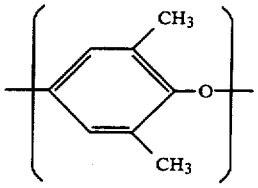

Mixture of the polyarylate and the polyether sulfone of the recurring units of the following formula

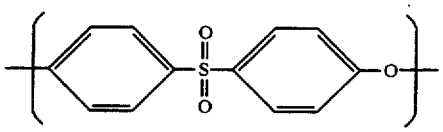

Mixture of the polyarylate and a polyester polycarbonate resin.

Mixture of the polyarylate and an aromatic liquid crystal polyester.

Mixture of the polyarylate resin and a polyether ketone resin.

Mixture of the polyarylate resin and a polyether ether ketone resin.

Moreover, resins obtained by copolymerizing, aside from the bisphenol, terephthalic acid and isophthalic acid (and derivatives thereof), aromatic dicarboxylic acids, such as polyethylene terephthalate, 2,6-naphthalenedicarboxylic acid and 4,4'-diphenyldicarboxylic acid, and derivatives thereof, and aromatic hydroxycarboxylic acids, such as paraacetoxybenzoic acid and 2-hydroxy-6-naphthoic acid, and derivatives thereof may also be used as the polyarylate-based resin when these resins contain not less than 70 wt % of a polyarylate resin component consisting of the above three ingredients.

The polyamide resins used in the present invention are those of the following general formula,

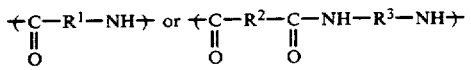

wherein $R^1$, $R^2$ and $R^3$ are independently an alkylene group having from 2 to 16 carbon atoms, and are prepared by Condensation reaction between diamines and dibasic acids, self-condensation of amino acids, or ring opening polymerization of lactams.

For instance, there can be mentioned nylon 6 prepared from ε-caprolactam or ε-aminocaproic acid, nylon 6–6 prepared from hexamethylenediamine and adipic acid, nylon 6–10 12 prepared from hexamethylenediamine and sebacic acid, nylon 6–12 prepared from hexamethylenediamine and dodecanoic acid, nylon 11 prepared from ω-aminoundecanoic acid, nylon 12 prepared from ω-laurolactam or ω-aminododecanoic acid, nylon 4–6 prepared from 1,4-diaminobutane and adipic acid, and the like. In view of the easy availability of the starting materials, nylon 6 and nylon 6–6 are preferred.

The polyamide-based resin is intended to mean those which contain not less than 70 wt % of the above-indicated polyamide resin or resins. For instance, there are mentioned so-called high impact nylons including blends of polyolefins and/or modified polyolefins with the polyamide resins, and those obtained by graft copolymerizing (meth)acrylic ester copolymers to the polyamide resins (Japanese Patent Publication No. 44-29262), and polyamide elastomers obtained by block copolymerization of polytetramethylene glycol with the polyamide resins. The modified polyolefins by copolymerization of α, β-unsaturated carboxylic acid or esters thereof, glycidyl ethers and metal salt derivatives, and by modifying by copolymerization or graft copolymerization of acid anhydrides. For example, there are mentioned ionomer resins obtained by ionizing ethylenemethacrylic acid (or ester) copolymers with Na, Zn, Mg or the like, modified EPDM obtained by graft copolymerizing ethylene-propylene-diene copolymers with maleic anhydride, those obtained by graft copolymerizing polypropylene or polyethylene with maleic anhydride, and ethylene-glycidyl methacrylate-vinyl acetate copolymers and styrene-maleic anhydride-acrylate copolymers.

Moreover, polymer blends of the polyamides with other resins such as ABS resins, acrylate copolymers, rubber-modified styrene-maleic anhydride copolymers and polyphenylene ethers are also usable as the polyamide-based resin used in the present invention provided that the polyamide component is contained in amounts not less than 70 wt %.

The epoxy resin used in the present invention is represented by the following general formula [1]

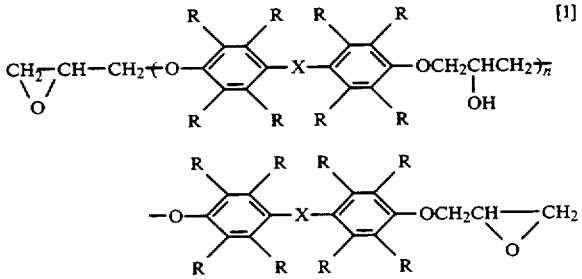

[1]

wherein X represents a direct bond, a lower alkylene group having from 1 to 4 carbon atoms, *a lower alkylidene group having from* 1 to 4 carbon atoms,

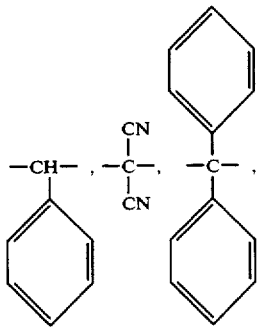

—$SO_2$—, —O—, or —S— wherein part or all of the hydrogen atoms of X may be substituted with a halogen atom if X represents any hydrocarbon defined above, R's independently represent a hydrogen atom, a halogen atom, a lower alkyl group having from 1 to 4 carbon atoms, and n is an integer of or over. This epoxy resin is obtained by a bisphenol and an epihalorohydrin such as epichlorohydrin. Examples of the bisphenol are those set forth with respect to the polyarylate resin. Of these, 2,2-bis(4-hydroxyphenyl)propane or bisphenol A is preferred because of the ease in availability of the starting materials.

In the formula [1], n which indicates the number of the repeating units in the formula should be 1 or over. If n is equal to zero, the adverse influence of the terminal epoxy group is apt to develop, with the tendency that the resultant resin composition is gelled, colored or decomposed. Especially, the melting temperature and viscosity increase considerably and thus, the molding becomes difficult. In order to bring out the effect of satisfactorily improving the impact strength, it is preferred that the terminal epoxy groups and the repeating polyether polyol units are present at an appropriate ratio. In this sense, a preferred range of n is from about 6 to 20. A preferred range of epoxy equivalents is from about 1000 to 3000 for bisphenol A-type epoxy resins.

The epoxy resins used in the present invention may contain, as copolymerized, a small amount of diols other than bisphenols, including aromatic diols such as 2,6-naphthalenediol, hydroquinone and the like, and aliphatic diols such as 1,4-butanediol, propylene glycol, ethylene glycol and the like.

Once again, the polyarylate-based resin and the polyamide-based resin used in the present invention should, respectively, contain a polyarylate resin component and a polyamide resin component in amounts not less than 70 wt %. If the content is less than 70 wt %, either or both of good impact strength and heat resistance to be imparted with the polyarylate-based resin will be lost, and either or both of good moldability and solvent resistance to be imparted with the polyamide-based resin will be lost. Eventually, one or more of the impact strength, heat resistance, moldability and solvent resistance which are the characteristics inherently imparted to the resin composition of the invention will be lowered.

With regard to the contents of the polyarylate-based resin and the polyamide-based resin, the former resin should be used in an amount of from 10 to 90 wt % and the latter resin should be used correspondingly in an amount of from 90 to 10 wt %. If great importance is placed on the heat resistance and impact strength, the polyarylate-based resin should be used in larger amounts. In contrast, if great importance is placed on the moldability, the polyamide-based resin should be used in larger amounts. In order to attain well-balanced heat resistance, impact strength and moldability properties, the compositional ratio should preferably be from 30 to 60 wt % of the polyarylate-based resin and from 70 to 40 wt % of the polyamide-based resin.

The amount of the epoxy resin should be in the range of from 0.1 to 15 parts by weight per 100 parts by weight of the mixture of the polyarylate-based resin and the polyamide-based resin. If the amount is less than 0.1 part by weight, the impact strength is not improved satisfactorily. Over 15 parts by weight, not only the resultant resin composition lowers in heat resistance, but also the melting temperature and viscosity increase, thus making molding operations difficult. Preferably, the amount is in the range of from 2 to 10 parts by weight.

For the production of the composition according to the first aspect of the invention, any method of melt kneading the polyarylate-based resin, polyamide-based resin and epoxy resin may be used without limitation. For instance, the melt kneading may be carried out by use of a two-roll mill, Banbury mixer, single-screw extruder, twin-screw extruder and the like. Alternatively, while kneading in an injection molding machine, the composition may be molded. Preferably, the single or twin-screw extruder of the high kneading type is used for kneading and molding. The kneading order of the respective ingredients for obtaining the composition of the first aspect of the invention is not critical. Preferably, the ingredients of the three components are added in the same time.

Additives and/or fillers may be further added to the resin composition of the invention. The additives may be antioxidants and thermal stabilizers such as copper halides, hindered phenols and the like, phosphorus working stabilizers, benzotriazole and hindered amine light stabilizers, plasticizers such as paraffins, higher fatty acids and esters thereof, metal salts and the like, lubricants such as silicone resins, fluorine resins and the like, flame retardants such as decabromodiphenyl ether, tetrabromobisphenol A, tetrachlorobisphenol A, aluminium hydroxide, antimony trioxide, ammonium phosphate, tricresyl phosphate, triethyl phosphate and the like, pigments, dyes and the like. The fillers may be talc, calcium carbonate, mica, wollastonite, ferrite, magnet powder of rare earth elements, glass fibers, carbon fibers, asbestos fibers, metallic fibers, aramide fibers, potassium titanate whiskers, and the like.

A second aspect of the invention is described.

According to the second aspect of the invention, there is provided a thermoplastic resin composition which comprises 100 parts by weight of a resin mixture consisting essentially of not less than 10 wt % of a polyarylate resin, not less than 20 wt % of a polyamide resin and from 3 to 60 wt % of a polyethylene terephthalate resin, and from 0.1 to 15 parts by weight of an epoxy resin of the following formula

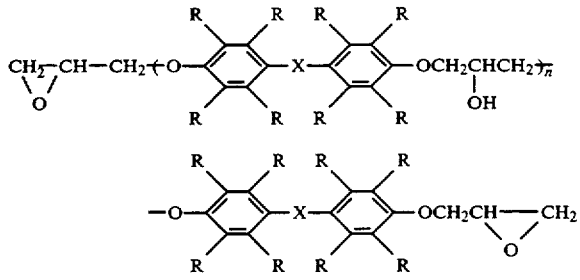

wherein X represents a direct bond, a lower alkylene group having from 1 to 4 carbon atoms, *a lower alkylidene group having from* 1 to 4 carbon atoms,

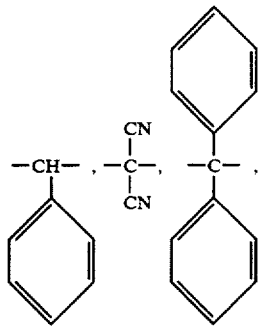

$-SO_2-$, *—O—, or —S— wherein part or all of the hydrogen atoms of X may be substituted with a halogen atom if X represents any hydrocarbon defined above, R's independently represent a hydrogen atom, a halogen atom, a lower alkyl group having from* 1 to 4 carbon atoms, and n is an integer of 1 or over.

The polyarylate resin, polyamide resin and epoxy resin used in the second aspect of the invention are, respectively, those defined in the second aspect of the invention.

The polyethylene terephthalate resin used in the second aspect of the invention is one which is prepared, by any known technique, from terephthalic acid and/or its derivative and ethylene glycol.

The polyarylate resin, polyethylene terephthalate resin and polyamide resin are, respectively, used in amounts of not less than 10 wt %, from 3 to 60 wt %, and not less than 20 wt %, each based on the total amount of these three resins. If the amount of the polyarylate resin is less than 10 wt %, the heat resistance and impact strength of the resultant resin composition become low. If the amount of the polyamide resin is less than 20 wt %, the moldability and solvent resistance are lowered. If the amount of the polyethylene terephthalate resin is less than 3 wt %, the moldability and rigidity (modulus of elasticity) of the resultant composition are lowered. Over 60 wt %, the heat resistance and impact strength are lowered.

An increasing amount of the polyarylate component results in an increase in the impact strength and heat resistance of the resultant composition. When the polyamide component increases in amount, better moldability and solvent resistance are obtained. If the polyethylene terephthalate component increases in amount, the moldability becomes better with an increase in rigidity. A preferable composition capable of imparting well-balanced properties such as heat resistance, impact strength, moldability, rigidity and solvent resistance comprises from 15 to 45 wt % of the polyarylate resin, from 45 to 65 wt % of the polyamide resin, and from 7 to 35 wt % of the polyethylene terephthalate.

The amount of the epoxy resin is generally in the range of from 0.1 to 15 parts by weight per 100 parts by weight of the mixture of the polyarylate resin, polyamide resin and polyethylene terephthalate resin. If the amount is less than 0.1 part by weight, the impact strength is not improved satisfactorily. Over 15 parts by weight, the resultant composition lowers in heat resistance, and the melting temperature and viscosity increase, making it difficult to mold such a composition. A preferable amount is in the range of from 2 to 10 parts by weight.

For the production of the composition according to this aspect, any technique of kneading the polyarylate resin, polyamide resin, polyethylene terephthalate resin and epoxy resin may be used without limitation. Favorable kneading and molding machines are those described with respect to the first aspect of the invention.

The kneading order for obtaining the composition according to the second embodiment of the invention is not critical. For instance, the polyarylate, polyamide, polyethylene terephthalate and epoxy resin may be simultaneously kneaded. Alternatively, two or more of the four components may be first kneaded, to which the other components are subsequently added. The optimum kneading order is such that the polyarylate and polyethylene terephthalate are first melt kneaded, followed by melt kneading the mixture, polyamide and epoxy resins.

As a matter of course, any additives and fillers as described with reference to the first aspect may be added to the resin composition of the second aspect of the invention.

EXAMPLES

The present invention is more particularly described by way of example, which should not be construed as limiting the present invention. Comparative examples are also shown.

First, starting materials used in the examples and comparative examples are illustrated.

1. Polyarylate-based resins (PAR-1 to PAR-8)

PAR-1: polyarylate resin obtained from a 1:1 mixture of terephthalic acid and isophthalic acid and bisphenol A(U-Polymer U-100, available from Unichika Co., Ltd.). The inherent viscosity was 0.65 when determined using a solvent of phenol and tetrachloroethane at a ratio by weight of 60:40 at a concentration of 0.25 g/dl at 23° C.

PAR-2~6: mixtures of 80 parts by weight of the polyarylate resin of PAR-1 and 20 parts of the respective resins indicated below which were melt kneaded by the use of a twin-screw extruder at a cylinder temperature of 300 to 360° C., thereby obtaining PAR-2, PAR-3, PAR-4, PAR-5 and PAR-6, respectively.

PAR-2: mixture with a polyphenylene sulfide resin (Riton, available from Philips Chem. Co., Ltd.).

PAR-3: mixture with a polyether ether ketone (Victrex 450G, available from Sumitomo Chemical Industries, Limited).

PAR-4: mixture with a polyether sulfone (Victrex 4100G, available from Sumitomo Chemical Industries, Limited).

PAR-5: mixture with polysulfone (UDEL P-1700, available from Amoco Chemical Inc.).

PAR-6: mixture with a wholly aromatic liquid crystal polyester obtained from 2-hydroxy-6-naphthoic acid and 4-hydroxybenzoic acid (Vectra A-950, available from Polyplastics Inc.).

PAR-7: polyarylate-based resin having the following structure and obtained by melt polymerization bisphenol A diacetate, terephthalic acid, isophthalic acid and paraacetoxybenzoic acid according to the process disclosed in U.S. Pat. No. 4075173.

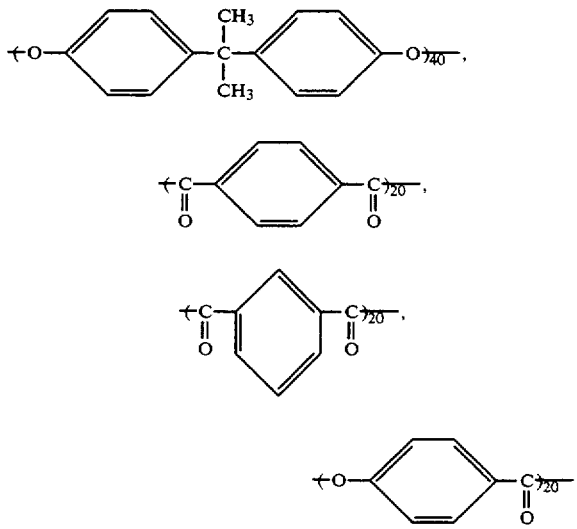

(the suffix values are by mole %)

The inherent viscosity was 0.68 as determined in the same manner as with PAR-1.

PAR-8: the polyarylate-based resin having the following structure was prepared by copolymerization of polyethylene terephthalate (inherent viscosity of 0.72) according to the process disclosed in Japanese Laid-open Patent Application No. 48-88193.

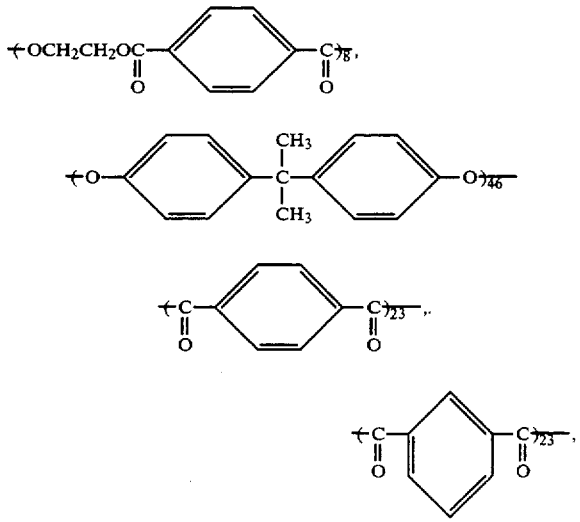

(the suffix values are by mole %)

The inherent viscosity was 0.70 as determined in the same manner as with PAR-1.

2. Polyamide-based resins (PA-1 to PA-3)

PA-1: nylon 6 (Amiran CM1017, available from Toray Limited).

PA-2: nylon 6-6 (Amiran CM3001, available from Toray Limited).

PA-3: obtained by melt kneading 80 parts by weight of nylon 6 used as PA-1 and 20 parts by weight of ethylene-acrylate-maleic anhydride copolymer (Bondine LX4110, available from Sumika CDF Chem. Co., Ltd.) by the use of a twin-screw extruder at a cylinder temperature of 240° C.

3 Third Ingredients (CP-1 to CP-8)

CP-1 to CP-6: epoxy resins (available from Danippon Ink and Chemicals, Inc.)

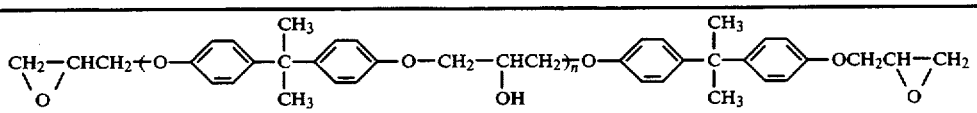

| Abbreviation | Commercial Name | Epoxy Equivalent | Approximate Number of n | Melting Point (°C.) |
|---|---|---|---|---|
| CP-1 | Epichlon 840 | 180 | n ≈ 0 | liquid (900 poises at 25° C.) |
| CP-2 | Epichlon 1050 | 450 | n ≈ 2 | 70 |
| CP-3 | Epichlon 4050 | 955 | n ≈ 5-6 | 102 |
| CP-4 | Epichlon 7050 | 1809 | n ≈ 12 | 130 |
| CP-5 | Epichlon 9055 | 2600 | n ≈ 17 | 152 |
| CP-6 | Epichlon 9155 | 4070 | n ≈ 28 | 155 |

*The epoxy equivalents in the epoxy resin was quantitatively determined by titration with perchloric acid to obtain the weight (g) of the resin per equivalent of the epoxy group.

CP-7: phenoxy resin (phenoxy PKHH, available from Union Carbide Co., Ltd.)

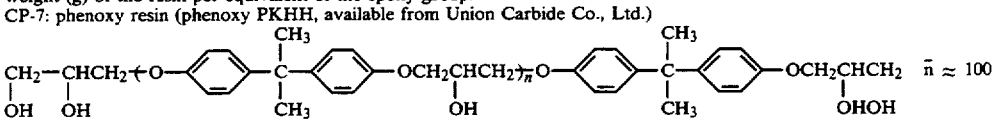

CP-8: Epichlon 9055 whose terminal epoxy groups were modified with diethanolamine

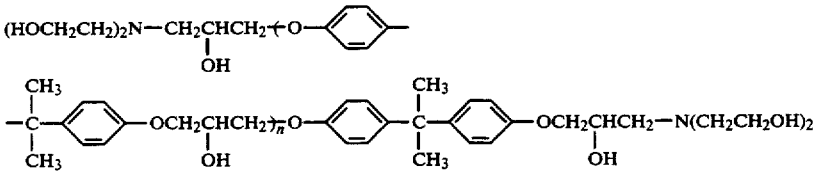

4. Polyethylene terephthalate resin (PE-1)

(PET resin TR-4550BH, available from Teijin Co., Ltd.). The inherent viscosity was 0.70 as determined in the same manner as with the polyarylate.

The physical properties were evaluated according to the following methods.

(1) Tensile test:the measurement was made according to ASTM D-638 at a pulling speed of 50 mm/minute to determine a tensile break strength, a tensile modulus and a tensile break energy (energy required before breakage).

(2) Izod impact test: the measurement was made according to ASTM D-256 using a thickness of ⅛ inches as notched.

(3) Heat distortion temperature: after annealing at 150° C. for 3 hours, the measurement was made according to ASTM D-648 at a thickness of ⅛ inches at a load of 18.6 kg.cm$^2$.

(4) Temperature at which the melt viscosity reaches 10,000 poises: the Koka-type flow tester CFT-500, made by Shimadzu Corporation, was used to successively measure the viscosity of resin by the use of a 0.5 mmØ×1.0 mm nozzle under conditions of a load of 10 kg and a heating rate of 6° C./minute thereby determining a temperature at which the melt viscosity reaches 10,000 poises. This is a kind of criterion for moldability of the resin and a criterion for the degree as to how the gelation reaction proceeds. More particularly, when the temperature is lower, a less degree of gelation proceeds with more ease in molding.

Examples 1 to 6 and Comparative Examples 1 and 2.

PAR-1 used as the polyarylate-based resin, PA-1 as the polyamide-based resin, and CP-5 as the third ingredient were mixed in different mixing ratios indicated in Table 1 and dried at 110° C. for 5 hours, followed by melt kneading and pelletizing in a twin-screw extruder at a cylinder temperature of 270° C. The resultant pellets of the respective mixtures were molded by means of an injection molding machine into ½×5×⅛ inch elongated test pieces and dumbbell specimens for ASTM tensile test. The respective moldings were evaluated with respect to the physical properties. The results are shown in Table 1.

Examples 7 to 11 and Comparative Examples 3 and 4

PAR-1 used as the polyarylate-based resin, PA-1 as the polyamide-based resin and CP-6 as the third ingredient were mixed at different mixing ratios indicated in Table 2. After drying at 110° C. for 5 hours, the mixtures were each melt kneaded and pelletized by means of a twin-screw extruder at an appropriate cylinder temperature ranging from 240 to 360° C. The resultant pellets were molded and evaluated in the same manner as in Example 1. The results are shown in Table 2.

Examples 12 to 14 and Comparative Examples 5 to 7

PAR-1 used as the polyarylate-based resin, PA-1 used as the polyamide-based resin and each of the third ingredients indicated in Table 3 were mixed at mixing ratios by weight of PAR-1/PA-1/third ingredient of 50/50/5, followed by kneading, molding and evaluation in the same manner as in Example 1. The results are shown in Table 3.

Examples 15 to 23

Each of the polyarylate-based resins and each of the polyamide-based resins, both indicated in Table 5, and CP-5 used as the third ingredient were mixed at mixing ratios by weight of polyarylate-based resin/polyamide-based resin/CP-5 of 50/50/5, followed by mixing, molding and evaluation in the same manner as in Example 1. The results are shown in Table 4.

Comparative example 8

6 kg of polycarbonate resin (Novarex 7025A, available from Mitsubishi Kasei Corp.), 4 kg of polyamide resin PA-1 and, as the third component, 500 g of CP-5 were mixed and the mixture was dried at 110° C. for 5 hours. The dried mixture was then melt-kneaded using a twin screw extruder at a cylinder temperature of 270° C. During the melt kneading, a part of the resins started to decompose inside the extruder and the decomposed substances gave out smoke, which resulted in the production of colored pellets. Molding of the pellets was attempted using an injection molding machine, but they were not moldable because they decomposed inside the cylinder of the injection molding machine.

Examples 24 to 29 and Comparative Examples 9 and 10

60 parts by weight of a polyarylate resin (PAR-1) and 40 parts by weight of a polyethylene terephthalate resin (PE-1) were mixed and dried at 110° C. for 5 hours. Thereafter, the mixture was melt kneaded and pelletized by means of a twin-screw extruder at a cylinder temperature of 300° C. 50 parts by weight of the mixture of the polyarylate resin and polyethylene terephthalate resin and 50 parts by weight of nylon 6 (PA-1) were mixed, to which an epoxy resin (CP-5) was added in different amount per 100 parts by weight of this mixture. After drying the respective mixtures, each mixture was melt kneaded and pelletized by means of a twin-screw extruder at a cylinder temperature of 270° C. The resultant pellets were molded by means of an injection molding machine into $\frac{1}{2}\times 1/5\times\frac{1}{8}$ inch elongated test pieces and dumbbell specimens for ASTM tensile test. The physical properties of the respective moldings were evaluated. The results are shown in Table 5.

From Table 5, it will be seen that the addition of small amounts of the epoxy resin results in a remarkable increase in the Izod impact strength and the tensile break energy. However, when the content of the epoxy resin exceeds 15 parts by weight, not only the impact strength and the heat distortion temperature are lowered, but also the moldability is worsened.

Examples 30 to 34 and Comparative Examples 11 to 16

A polyarylate resin (PAR-1), a polyethylene terephthalate resin (PE-1), nylon 6 (PA-1) and an epoxy resin (CP-5) were mixed in different mixing ratios indicated in Table 6, followed by pelletization in the same kneading order and manner as in Example 24, injection molding and evaluation of the physical properties. The results are shown in Table 6.

Examples 35 to 41 and Comparative Examples 17 to 21

Starting materials at different mixing ratios as indicated in Table 7 were pelletized in the same manner as in Example 24 wherein the polyarylate resin and polyethylene terephthalate were initially melt kneaded, to which the other two ingredients were added and melt kneaded for pelletization, followed by injection molding and evaluation of the physical properties. The results are shown in Table 7.

TABLE 1

| | Composition PAR-1/PA-1/CP-5 (ratios by weight) | Strength (kg/cm²) | Tensile Test Modulus (kg/cm²) | Energy (kg-cm) | Melt Temp. of 10,000 Poises (°C.) | Izod Impact Strength (kg-cm/cm) | Heat Distortion Temperature (°C.) |
|---|---|---|---|---|---|---|---|
| Comparative Example 1 | 50/50/0 | 420 | 21100 | 220 | 272 | 1.5 | 165 |
| Example 1 | 50/50/1 | 607 | 21600 | 680 | 301 | 4.7 | 165 |
| Example 2 | 50/50/3 | 649 | 21600 | 1700 | 312 | 11.5 | 162 |
| Example 3 | 50/50/5 | 659 | 22800 | 1740 | 323 | 12.5 | 160 |
| Example 4 | 50/50/7 | 666 | 22300 | 1200 | 335 | 13.0 | 155 |
| Example 5 | 50/50/10 | 687 | 22300 | 570 | 342 | 8.1 | 153 |
| Example 6 | 50/50/15 | 701 | 23100 | 170 | 380 | 7.2 | 128 |
| Comparative Example 2 | 50/50/20 | 680 | 23000 | 120 | >400 | 6.6 | 119 |

TABLE 2

| | Composition PAR-1/PA-1/CP-5 (ratios by weight) | Strength (kg/cm²) | Tensile Test Modulus (kg/cm²) | Energy (°C.) | Melt Temp. of 10,000 Poises (kg-cm) | Izod Impact Strength (kg-cm/cm) | Heat Distortion Temperature (°C.) |
|---|---|---|---|---|---|---|---|
| Comparative Example 3 | 0/100/5 | 629 | 23800 | 650 | 237 | 4.3 | 71 |
| Example 7 | 20/80/5 | 619 | 23400 | 800 | 290 | 6.5 | 132 |
| Example 8 | 40/60/5 | 661 | 22900 | 1400 | 308 | 11.8 | 154 |
| Example 9 | 50/50/5 | 666 | 22100 | 1600 | 319 | 12.0 | 157 |
| Example 10 | 60/40/5 | 643 | 21500 | 1200 | 325 | 12.5 | 159 |
| Example 11 | 80/20/5 | 649 | 21800 | 700 | 340 | 8.0 | 167 |
| Comparative Example 4 | 100/0/5 | 741 | 22100 | 250 | 352 | 15.8 | 170 |

TABLE 3

| | Third Ingredient | Strength (kg/cm²) | Tensile Test Modulus (kg/cm²) | Energy (kg-cm) | Melt Temp. of 10,000 Poises (°C.) | Izod Impact Strength (kg-cm/cm) | Heat Distortion Temperature (°C.) |
|---|---|---|---|---|---|---|---|
| Example 12 | CP-2 | 720 | 24000 | 420 | 335 | 5.0 | 140 |
| Example 13 | CP-3 | 717 | 23900 | 550 | 314 | 6.3 | 142 |
| Example 14 | CP-4 | 677 | 22900 | 800 | 323 | 11.3 | 151 |
| Comparative Example 5 | CP-1 | impossible to mold dumbbell | | | >400 | 3.1 | 138 |
| Comparative Example 6 | CP-7 | 604 | 22300 | 65 | 299 | 2.1 | 120 |
| Comparative Example 7 | CP-8 | 614 | 22500 | 70 | 300 | 3.7 | 129 |

TABLE 4

| | Starting Material | | | | | | | | |
|---|---|---|---|---|---|---|---|---|---|
| | Poly-arylate | Poly-amide | Third Compo-nent | Strength (kg/cm²) | Tensile Test Modulus (kg/cm²) | Break Energy (kg-cm) | Melt Temp. of 10,000 Poises (°C.) | Izod Impact Strength (kg-cm/cm) | Heat Distortion Temperature (°C.) |
| Example 15 | PAR-2 | PA-1 | CP-5 | 609 | 22900 | 550 | 320 | 6.7 | 130 |
| Example 16 | PAR-3 | PA-1 | CP-5 | 596 | 21800 | 880 | 391 | 4.6 | 154 |
| Example 17 | PAR-4 | PA-1 | CP-5 | 622 | 23200 | 1600 | 316 | 8.1 | 147 |
| Example 18 | PAR-5 | PA-1 | CP-5 | 610 | 22000 | 2500 | 320 | 6.8 | 155 |
| Example 19 | PAR-6 | PA-1 | CP-5 | 601 | 22900 | 600 | 321 | 8.4 | 160 |
| Example 20 | PAR-7 | PA-1 | CP-5 | 650 | 22500 | 1850 | 320 | 13.0 | 159 |
| Example 21 | PAR-8 | PA-1 | CP-5 | 645 | 22300 | 1900 | 315 | 12.6 | 158 |
| Example 22 | PAR-1 | PA-2 | CP-5 | 699 | 23700 | 1100 | 313 | 8.0 | 161 |
| Example 23 | PAR-1 | PA-3 | CP-5 | 524 | 16600 | 800 | 380 | 6.8 | 147 |

TABLE 5

| | Composition PAR-1/PA-1/CP-5 (ratios by weight) | Strength (kg/cm²) | Tensile Test Modulus (kg/cm²) | Energy (kg-cm) | Melt Temp. of 10,000 Poises (°C.) | Izod Impact Strength (kg-cm/cm) | Heat Distortion Temperature (°C.) |
|---|---|---|---|---|---|---|---|
| Comparative Example 9 | 30/20/50/0 | 497 | 23900 | 30 | 266 | 2.6 | 115 |
| Example 24 | 30/20/50/1 | 549 | 24400 | 800 | 272 | 3.3 | 116 |
| Example 25 | 30/20/50/3 | 724 | 25100 | 1500 | 283 | 4.5 | 122 |
| Example 26 | 30/20/50/5 | 745 | 25200 | 2640 | 296 | 6.6 | 118 |
| Example 27 | 30/20/50/7 | 749 | 25300 | 1800 | 310 | 6.5 | 115 |
| Example 28 | 30/20/50/10 | 752 | 25400 | 1550 | 332 | 6.3 | 105 |
| Example 29 | 30/20/50/15 | 747 | 25700 | 1410 | 380 | 5.2 | 102 |
| Comparative Example 10 | 30/20/50/20 | 752 | 25700 | 1310 | >400 | 3.3 | 95 |

PAR-1: polyarylate resin
PE-1: polyethylene terephthalate resin
PA-1: polyamide resin
CP-5: epoxy resin

TABLE 6

| | Composition PAR-1/PA-1/CP-5 (ratios by weight) | Strength (kg/cm²) | Tensile Test Modulus (kg/cm²) | Energy (kg-cm) | Melt Temp. of 10,000 Poises (°C.) | Izod Impact Strength (kg-cm/cm) | Heat Distortion Temperature (°C.) |
|---|---|---|---|---|---|---|---|
| Comparative Example 11 | 0/50/50/5 | 646 | 25500 | 400 | 290 | 2.5 | 86 |
| Comparative Example 12 | 5/45/50/5 | 612 | 24900 | 60 | 301 | 2.8 | 87 |
| Comparative Example 13 | 9/41/50/5 | 585 | 24500 | 60 | 303 | 3.8 | 87 |
| Example 30 | 15/35/50/5 | 650 | 24400 | 930 | 308 | 7.1 | 92 |
| Example 31 | 25/25/50/5 | 710 | 24400 | 2610 | 312 | 7.4 | 102 |
| Example 32 | 35/15/50/5 | 740 | 25200 | 2380 | 316 | 5.4 | 128 |
| Example 33 | 40/10/50/5 | 730 | 24500 | 2040 | 319 | 6.4 | 134 |
| Example 34 | 45/5/50/5 | 690 | 23300 | 2110 | 320 | 9.5 | 145 |
| Comparative Example 14 | 50/0/50/5 | 660 | 22800 | 1740 | 323 | 12.5 | 155 |
| Comparative Example 15 | 60/30/10/5 | 716 | 23300 | 1040 | 363 | 12.1 | 138 |
| Comparative | 15/70/15/5 | 592 | 21900 | 90 | 295 | 2.8 | 94 |

TABLE 6-continued

| | Composition PAR-1/PA-1/CP-5 (ratios by weight) | Strength (kg/cm²) | Tensile Test Modulus (kg/cm²) | Energy (kg-cm) | Melt Temp. of 10,000 Poises (°C.) | Izod Impact Strength (kg-cm/cm) | Heat Distortion Temperature (°C.) |
|---|---|---|---|---|---|---|---|
| Example 16 | | | | | | | |

PAR-1: polyarylate resin
PE-1: polyethylene terephthalate resin
PA-1: polyamide resin

TABLE 7

| | Composition (ratios by weight) | Strength (kg/cm²) | Tensile Test Modulus (kg/cm²) | Break Energy (kg-cm) | Melt Temp. of 10,000 Poises (°C.0 | Izod Impact Strength (kg-cm/cm) | Heat Distortion Temperature (°C.) |
|---|---|---|---|---|---|---|---|
| Comparative Example 17 | PAR-1/PE-1/PA-1/CP-1 = 30/20/50/5 | impossible to mold dumbbell | | | >400 | 3.8 | 112 |
| Example 35 | PAR-1/PE-1/PA-1/CP-2 = 30/20/50/5 | 748 | 25700 | 1860 | 343 | 6.5 | 114 |
| Example 36 | PAR-1/PE-1/PA-1/CP-3 = 30/20/50/5 | 742 | 25200 | 1930 | 337 | 6.8 | 115 |
| Example 37 | PAR-1/PE-1/PA-1/CP-4 = 30/20/50/5 | 736 | 24900 | 2030 | 320 | 7.1 | 115 |
| Example 38 | PAR-1/PE-1/PA-1/CP-6 = 30/20/50/5 | 728 | 25300 | 120 | 302 | 4.6 | 118 |
| Comparative Example 18 | PAR-1/PE-1/PA-1/CP-7 = 30/20/50/5 | 621 | 23400 | 70 | 270 | 3.5 | 108 |
| Comparative Example 19 | PAR-1/PE-1/PA-1/CP-8 = 30/20/50/5 | 586 | 24800 | 80 | 272 | 3.3 | 106 |
| Example 39 | PAR-1/PE-1/PA-2/CP-5 = 30/20/50/5 | 775 | 26300 | 810 | 318 | 6.0 | 125 |
| Comparative Example 20 | PAR-1/PE-1/PA-2 = 45/5/50 | 580 | 22700 | 70 | 269 | 1.7 | 134 |
| Example 40 | PAR-1/PE-1/PA-2/CP-6 = 45/5/50/5 | 660 | 23700 | 730 | 309 | 7.5 | 113 |
| Comparative Example 21 | PAR-1/PE-1/PA-1 = 45/5/50 | 420 | 19500 | 30 | 268 | 2.7 | 137 |
| Example 41 | PAR-1/PE-1/PA-1/CP-6 = 45/5/50/5 | 570 | 19400 | 660 | 305 | 8.5 | 111 |

PAR-1: polyarylate resin
PE-1: polyethylene terephthalate resin
PA-1, PA-2: polyamide resins
CP-1 to CP-6: epoxy resins
CP-7: phenoxy resin
CP-8: modified epoxy resin The resin composition according to the present invention has especially good moldability, heat resistance, impact strength, solvent resistance and high rigidity and are thus well balanced in the physical properties. When making use of these characteristic features, the resin composition of this aspect has utility optimally as plastics for outer plates of automobile having the capability of paint baking, switches, knobs, housings of electronic and electric instruments which are exposed to intense heat, containers and housing instruments which are exposed to chemical compounds.

What is claimed is:

1. A thermoplastic resin composition which comprises 100 parts by weight of a resin composition which comprises 100 parts by weight of a resin mixture consisting essentially of not less than 10 wt % of a polyarylate resin, not less than 20 wt % of a polyamide resin and from 3 to 60 wt % of a polyethylene terephthalate resin, and from 0.1 to 15 parts by weight of an epoxy resin of the following formula [1]

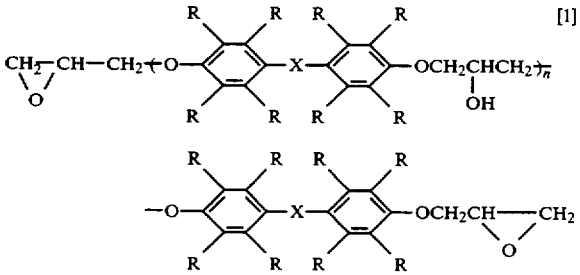

[1]

wherein X represents a direct bond, a lower alkylene group having from 1 to 4 carbon atoms, *a lower alkylidene group having from* 1 to 4 carbon atoms,

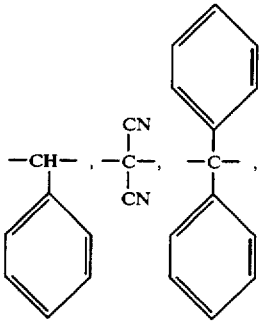

$-SO_2-$, —O—, or —S— wherein part or all of the hydrogen atoms of X may be substituted with a halogen atom if X represents any hydrocarbon defined above, R's independently represent a hydrogen atom, a halogen atom, a lower alkyl group having from 1 to 4 carbon atoms, and n is an integer of 1 to 20.

2. A thermoplastic resin composition according to claim 1, wherein, in the formula [1], n is from 6 to 20.

3. A thermoplastic resin composition according to claim 1, wherein the amount of said polyarylate resin is from 15 to 45 wt %, the amount of said polyamide resin is from 45 to 65 wt % and the amount of said polyethylene terephthalate resin is from 7 to 35 wt % and said epoxy resin is from 2 to 10 parts by weight per 100 parts by weight of the total of said polyarylate resin, said polyamide resin and said polyethylene terephthalate resin.

* * * * *